US00PP26167P3

(12) United States Plant Patent
Olesen

(10) Patent No.: US PP26,167 P3
(45) Date of Patent: Dec. 1, 2015

(54) MINIATURE ROSE PLANT NAMED 'POULPAL053'

(50) Latin Name: ***Rosa* hybrid**
Varietal Denomination: Poulpal053

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 124 days.

(21) Appl. No.: 13/986,921

(22) Filed: Jun. 14, 2013

(65) Prior Publication Data

US 2014/0373212 P1 Dec. 18, 2014

(51) Int. Cl.
*A01H 5/02* (2006.01)

(52) U.S. Cl.
USPC ..... Plt./115

(58) Field of Classification Search
USPC ..... Plt./101, 115, 116
See application file for complete search history.

(56) References Cited

PUBLICATIONS

UPOV-PLUTO Plant Variety Database, International Union for Protection of New Varieties of Plants, Jan. 29, 2015, obtained for cultiver 'Poulpal053' (1 page total).*
Poulsen Roser A/S catalog; Retrieved from the Internet http://www.poulsenroser.com (1 page total).*

* cited by examiner

*Primary Examiner* — Susan McCormick Ewoldt

(57) ABSTRACT

A new miniature rose plant that has abundant, orange red flowers and attractive foliage. The variety successfully propagates from softwood cuttings and is suitable for year-round production in commercial glasshouses. This new and distinct variety has shown to be uniform and stable in the resulting generations from asexual propagation.

2 Drawing Sheets

Botanical designation: *Rosa* hybrid.
Variety denomination: 'Poulpal053'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2007 and the resulting seeds were planted in a controlled environment in Fredensborg, Denmark. The new variety, named 'Poulpal053', originated as a single seedling from the stated cross.

The new variety may be distinguished from its male pollen parent and female seed parent primarily by flower coloration and growth habit. The female seed parent is 25 cm in growth height, while the claimed plant is 30 cm in height. The male pollen parent has apricot colored flowers, while the claimed variety has orange red flowers.

The objective of the hybridization of this rose variety for commercial culture was to create a new and distinct variety with unique qualities, such as:

1. Uniform and abundant orange red flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpal053' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpal053' was selected by the inventor as a single plant from the progeny of the hybridization in 2007.

Asexual reproduction of 'Poulpal053' by cuttings was first done by Mogens N. Olesen in the nursery in Fredensborg, Denmark in 2008. This initial and other subsequent propagations conducted in controlled environments have demonstrated that the characteristics of 'Poulpal053' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal053'.

Specifically illustrated in FIG. 1 are flower in parts,
FIG. 2 are leaves and stems.
Illustrated plants are 3 months of age.

DETAILED DESCRIPTION OF THE VARIETY

Figure 1:
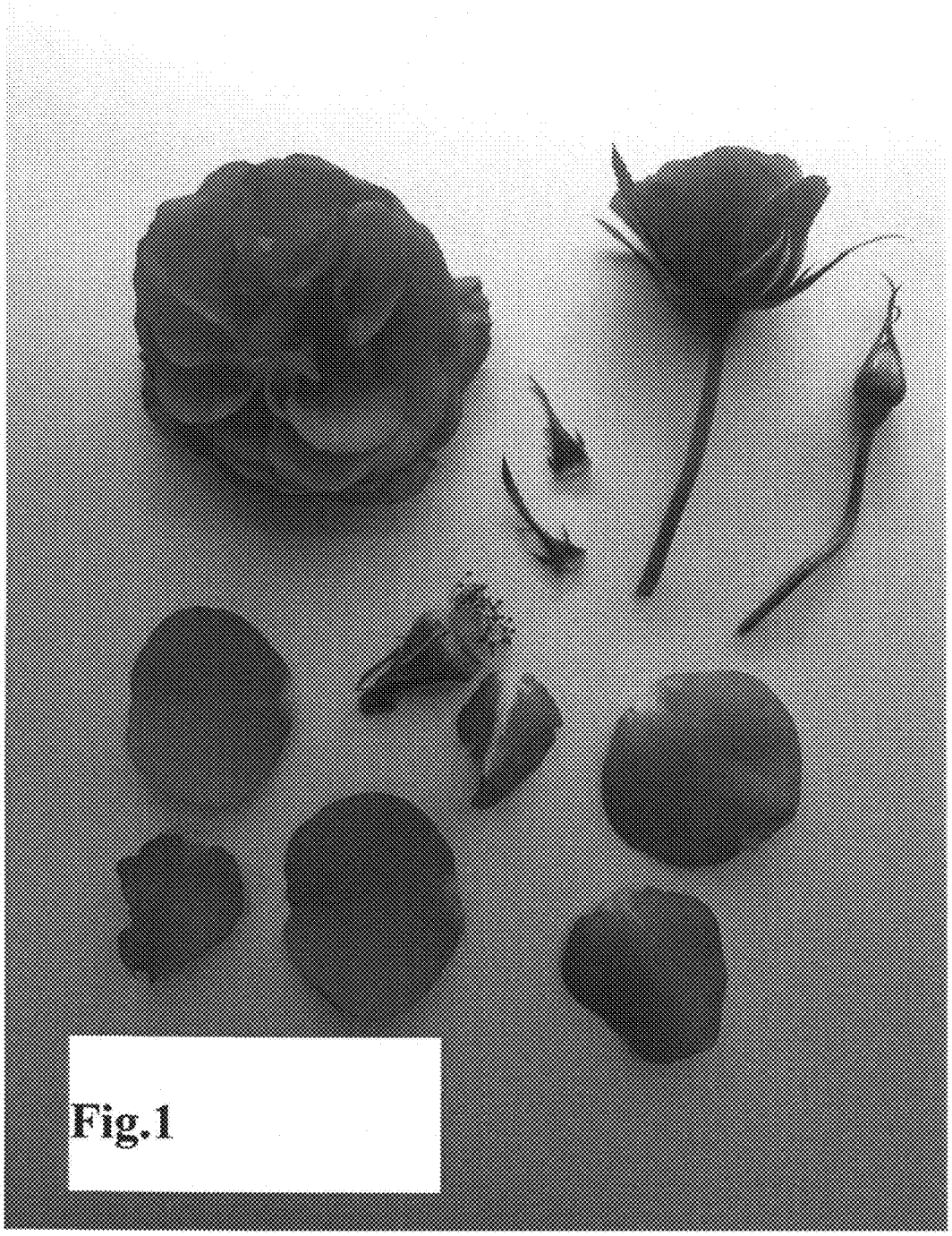
Figure 2:
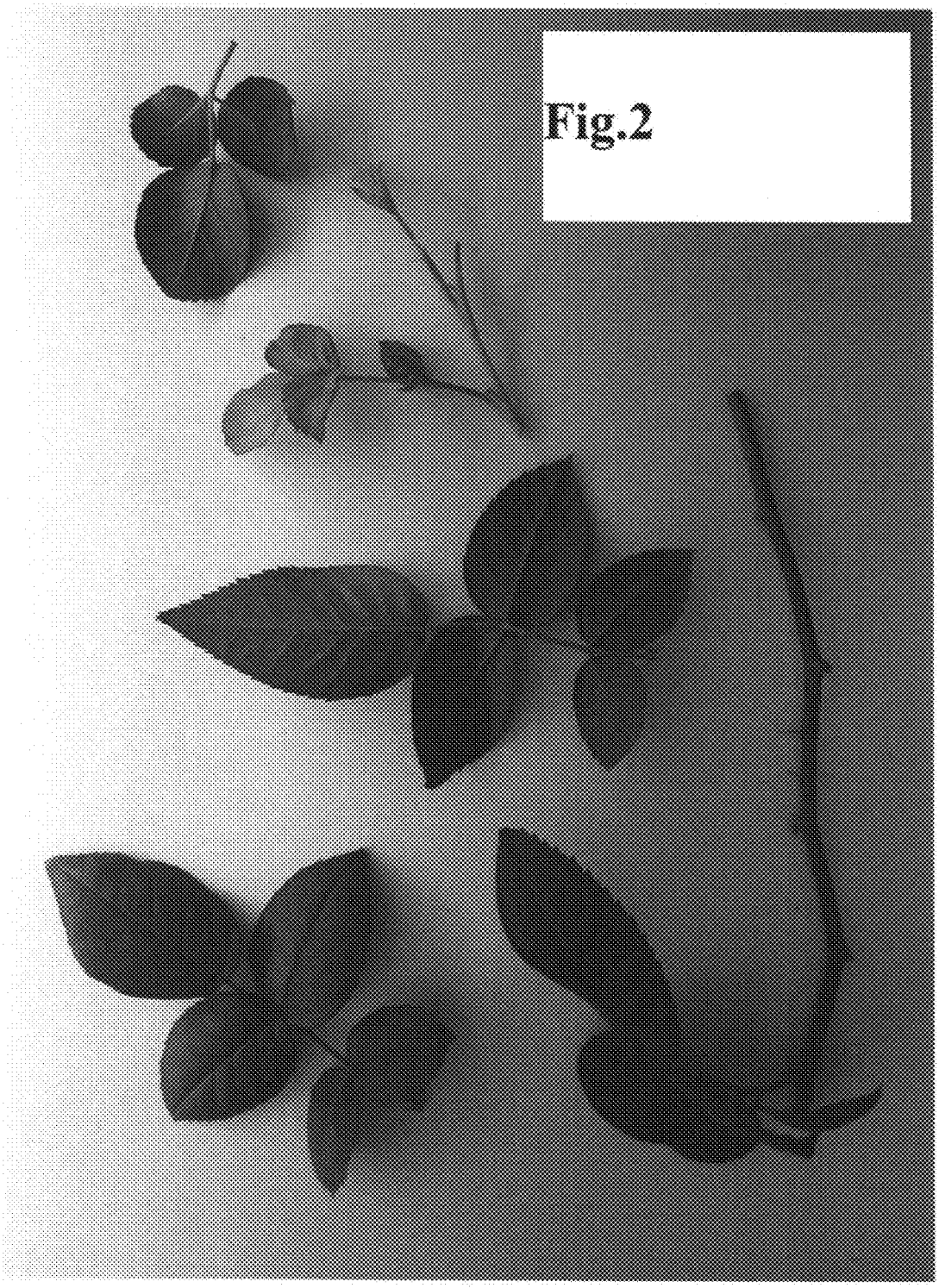

The following is a description of 'Poulpal053', as observed in its growth in glasshouses in Burlington, Ontario, Canada.

Observed plants are 3 months of age and were cultivated in 15 cm pots. Color references are made using The Royal Horticultural Society (London, England) Colour Chart, 2001, except where common terms of color are used.

For a comparison, several physical characteristics of the rose variety 'Poulpal024', U.S. Plant Pat. No. 17,031 are compared to 'Poulpal053' in Chart 1.

CHART 1

| | 'Poulpal053' | 'Poulpal024' |
|---|---|---|
| Petalage: | 17 petals | 55 to 60 petals |
| Flower Diameter: | 65 mm | 60 to 65 mm |
| General Tonality of Flower Color: | Red Group 38A with intonations of Red-Purple Group 58B | Red Group 41A |

FLOWER AND FLOWER BUD

Blooming habit: Continuous.

Flower bud:

*Size.*—Upon opening, 20 mm in length from base of receptacle to end of bud. 10 mm in diameter.

*Bud form.*—Ovate.

*Bud color.*—As sepals unfold, petals are Red Group 53C.

*Sepals.*—Upper Surface: Color: Green Group 138 B. Texture: Smooth and pubescent. Lower Surface: Color: Yellow Green Group 144A. Texture: Smooth. Shape: Apex: Cirrhose. Base: Flat at union with receptacle. Margins: Margins have moderate foliaceous appendages on three of the five sepals. Size: 23 mm long by 7 mm wide.

*Receptacle.*—Surface Texture: Smooth. Shape: Campanulate. Size: 6 mm tall and 6 mm wide. Color: Yellow Green Group 144A.

*Pedicel.*—Surface: Smooth. Length: 40 mm on average. Diameter: Generally 4 mm. Color: Yellow-Green Group 144A. Strength: Strong.

*Borne.*—Singly.

Flower bloom:

*Fragrance.*—Light floral scent.

*Duration.*—As a pot plant, flowers last up to 28 days.

*Size.*—Flower diameter is 65 mm when open. Flower depth is 30 mm.

*Form.*—General shape is a hybrid tea with a high pointed center. As the flower opens it becomes an open cup with the flower reproductive parts exposed.

*Shape of flower, side view.*—Upon opening, the upper portion is flat. The lower portion is flat.

Petalage: Under normal conditions, flowers have 17 petals total. No petaloids.

Color:

*General tonality.*—On open flower Red Group 38A with intonations of Red-Purple Group 58B.

*Upon opening, petals.*—Inner and outer petals are Orange Red Group 32C with intonations of Orange Group 29A on the upper surface. Red Group 53C on the lower surface. At the base of the petal, the upper surface is Yellow Group 13C and the lower surface is Yellow Group 12C.

*After opening, petals.*—Innermost and outer petals are Orange 29B with marginal intonations of Orange Red Group N34C on the upper surface. Red Group 53C to 53B. At the base of the petal, the upper surface is Yellow 13C and the lower surface is Yellow Group 8B.

Petals:

*Petal reflex.*—None.

*Margin.*—Slight cleft at the center of the apex.

*Shape.*—Generally rounded. Apex shape: Rounded. Base shape: Rounded.

*Size.*—35 mm (l) by 40 mm (w).

*Texture.*—Smooth.

*Thickness.*—Average.

Petaloids: None observed.

Reproductive organs:

*Pollen.*—None Observed.

*Anthers.*—Size: 1.5 mm long. Color: Greyed-Orange Group 166C. Quantity: 40 on average.

*Filaments.*—Color: Yellow Group 7B. Length: About 6 mm.

*Pistils.*—Length: About 4 mm long. Quantity: 20 on average.

*Stigmas.*—Inferior relative to the length of the filaments and the height of the anthers. Color: Yellow Group 11A.

*Styles.*—Color: Yellow Group 11A.

*Seed formation.*—Not observed.

PLANT

Plant growth: Upright. Plants are 30 cm in height, and 25 cm wide.

Stems:

*Color.*—Juvenile growth: Yellow-Green Group 145A. Mature growth: Yellow-Green Group 146A.

*Length.*—Canes are 18 cm from the base of the plant to the flowering portion.

*Diameter.*—3 to 4 mm.

*Internodes.*—On mature canes, there is an average distance of 35 mm between nodes.

*Surface texture.*—Young and mature wood is smooth.

Prickles:

*Incidence.*—3 per 10 cm of stem.

*Size.*—Average length: 4 mm.

*Color.*—Juvenile and mature prickles are Greyed-Yellow Group 162B.

*Shape.*—Linear.

Plant foliage:

*Compound leaf size.*—100 mm (l) by 75 mm (w).

*Quantity.*—3 leaves per 10 cm of stem.

*Color of juvenile foliage.*—Upper Leaf Surface: Yellow-Green Group 145A with intonations of Greyed-Orange Group 165A at margins. Lower Leaf Surface: Yellow-Green Group 144B with marginal intonations of Greyed-Orange Group 166A.

*Color of mature foliage.*—Upper Leaf Surface: Yellow-Green Group 147A. Lower Leaf Surface: Yellow-Green Group 147B.

Plant leaves and leaflets:

*Stipules.*—Size: About 5 mm in length. Shape: Linear, slightly broad based with outward extending apecies. Margins: Finely serrated with few stipitate glands. Color: Yellow-Green Group 144A.

*Petiole.*—Length: 16 mm on average. Diameter: About 2 mm. Upper surface: Yellow-Green Group 144A with intonations of Greyed-Purple Group 183A. Lower surface: Yellow-Green Group 144B.

*Rachis.*—Length: 30 mm on average. Diameter: About 2 mm. Upper surface: Yellow-Green Group 144A with intonations of Greyed-Purple Group 183A. Lower surface: Yellow-Green Group 144B. Small prickles.

*Leaflet.*—Number of leaflets: 5 on normal leaves in middle of the stem. Size: 50 mm in length by 30 mm wide. Margin: Serrate. General Shape: Elliptical. Apex Shape: Acute. Base Shape: Round. Texture: Smooth. Arrangement: Odd pinnate. Venation: Reticulate. Leaf Gloss: Glossy.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the miniature class named 'Poulpal053', substantially as illustrated and described herein, due to its abundant, orange red flowers, vigorous growth, compact habit, suitability for production from softwood cuttings in pots, and durable flowers and foliage that make the variety suitable for distribution in the floral industry.

* * * * *